(12) United States Patent
Vogt

(10) Patent No.: US 12,171,717 B2
(45) Date of Patent: Dec. 24, 2024

(54) NEUROTOXIN PREFILLED VIAL

(71) Applicant: Merz Pharma Gmbh & Co. KGaA, Frankfurt am Main (DE)

(72) Inventor: Markus Vogt, Frankfurt am Main (DE)

(73) Assignee: Merz Pharma GmbH & Co. KGaA, Frankfurt am Main (DE)

( * ) Notice: Subject to any disclaimer, the term of this patent is extended or adjusted under 35 U.S.C. 154(b) by 735 days.

(21) Appl. No.: 17/282,397

(22) PCT Filed: Oct. 7, 2019

(86) PCT No.: PCT/EP2019/077042
§ 371 (c)(1),
(2) Date: Apr. 2, 2021

(87) PCT Pub. No.: WO2020/074419
PCT Pub. Date: Apr. 16, 2020

(65) Prior Publication Data
US 2021/0338528 A1    Nov. 4, 2021

(30) Foreign Application Priority Data
Oct. 8, 2018   (EP) .................................... 18199175

(51) Int. Cl.
*A61J 1/14*     (2023.01)
*B65B 3/00*    (2006.01)
*B65B 31/02*  (2006.01)

(52) U.S. Cl.
CPC ........... *A61J 1/1468* (2015.05); *A61J 1/1406* (2013.01); *B65B 3/003* (2013.01); *B65B 31/027* (2013.01)

(58) Field of Classification Search
CPC .......... A61J 1/1468; A61J 1/1406; A61J 1/00; A61J 1/14; A61J 1/1412; A61J 1/06; A61J 1/2096; A61J 1/2089; B65B 3/003; B65B 31/027; B32B 2250/03; B32B 1/00; B32B 2307/7145; B32B 2307/7244; B32B 2439/40; B32B 2439/80; B32B 27/306; A61M 5/28; A61K 38/4893

See application file for complete search history.

(56) References Cited

U.S. PATENT DOCUMENTS

| | | | |
|---|---|---|---|
| 6,992,218 B2 * | 1/2006 | Dietlin | A61K 9/0019 564/4 |
| 2012/0135658 A1 * | 5/2012 | Stone | B32B 5/08 428/458 |
| 2015/0299851 A1 | 10/2015 | Bicker et al. | |
| 2018/0015225 A1 | 1/2018 | Vogt | |
| 2018/0125756 A1 * | 5/2018 | Gerrish | C03C 3/091 |
| 2020/0354550 A1 * | 11/2020 | Takeuchi | B32B 27/325 |

FOREIGN PATENT DOCUMENTS

| | | | | |
|---|---|---|---|---|
| JP | 2018-126313 A | 8/2018 | | |
| WO | 00/15245 A2 | 3/2000 | | |
| WO | WO-2016124213 A1 * | 8/2016 | ............... | A61J 1/06 |
| WO | WO-2017100182 A1 * | 6/2017 | ........... | B32B 15/082 |

OTHER PUBLICATIONS

PCT International Search Report for PCT/EP2019/077042, mailed Jan. 8, 2020.
International Written Opinion for International Application No. PCT/EP2019/077042 mailed Jan. 8, 2020.

* cited by examiner

*Primary Examiner* — Catharine L Anderson
*Assistant Examiner* — Erin A Kim
(74) *Attorney, Agent, or Firm* — McBee Moore & Vanik IP, LLC

(57) ABSTRACT

The present invention relates to a vial that is at least partially filled with an aqueous formulation of a neurotoxin, preferably botulinum toxin, to the manufacture of the vial and to the use thereof. The aqueous formulation of a neurotoxin is stable in the vial for a prolonged period of time.

14 Claims, No Drawings

NEUROTOXIN PREFILLED VIAL

CROSS-REFERENCE TO RELATED APPLICATIONS

This application is the National Stage entry of International Application No. PCT/EP2019/077042, filed 7 Oct. 2019, which claims priority to European Patent Application No. 18199175.3, filed 8 Oct. 2018.

BACKGROUND

Field

FIELD OF THE INVENTION

The present invention relates to a vial that is at least partially filled with an aqueous formulation of a neurotoxin, preferably botulinum toxin, to the manufacture of the vial and to the use of thereof. The aqueous formulation of a neurotoxin is stable in the vial for a prolonged period of time.

Description of Related Art

The stability of pharmaceutical products is of paramount importance to ensure safe and efficacious use for a sufficiently long time period. Unfortunately, the performance (safety, reliability, and efficacy) of most pharmaceutical products deteriorates over time. The causes of drug deterioration include chemical degradation (e.g., hydrolysis, oxidation, reduction and racemization), microbial contamination, and other mechanisms (e.g., precipitation).

Protein active ingredients are often of a labile nature and inherently instable. This leads to loss of biological activity during production, reconstitution and/or storage of protein-containing pharmaceutical compositions. These problems may be due to chemical instability, resulting in bond formation or cleavage (e.g., hydrolysis, oxidation, racemization, β-elimination and disulfide exchange), and/or due to physical instability of the second or higher-order structure of proteins without covalent bond-breaking modification (e.g., denaturation, adsorption to surfaces, and non-covalent self-aggregation).

Since degradation reactions are generally fastest in aqueous formulation and slowest in solid dosage forms, protein active ingredients are often formulated as lyophilized (i.e., freeze-dried) products. However, lyophilized products have generally to be reconstituted with a pharmaceutically acceptable liquid (e.g., saline) prior to use, which is a potential source of errors. Therefore, lyophilized pharmaceutical products are considered less convenient than other ready-to-use dosage forms. Further, lyophilized products are far more expensive and time-consuming to manufacture compared to solution formulations. Moreover, mismanagement can occur during the reconstitution process resulting in inaccurate dosing or sterility issues.

In view of the above, aqueous formulations of protein active ingredients are generally highly sought after. However, aqueous formulations entail a number of drawbacks. In particular, it has been shown that degradation reactions are generally fast in aqueous formulations. On the one hand, this is due to the labile nature of the protein active ingredient itself. On the other hand, also the packing material used for packaging the aqueous formulation of the protein active ingredient plays a significant role in the degradation of the protein active ingredient. For example, packaging materials made of plastic (e.g., vials, syringes) are known to destabilize proteins (e.g., neurotoxins), which is believed to be due to the nature of the material itself as well as due to additives used in packaging material production (e.g., plasticizers). A further disadvantage of plastic materials is their gas-permeable nature so that oxygen may diffuse into the aqueous formulation of the protein active ingredient, which very often destabilizes the protein active ingredient (e.g., a neurotoxin).

Therefore, glass is typically used and considered as the current industry standard for packaging of protein active ingredients. However, glass is not free of disadvantages. For example, glass has a high risk of breakage and may influence the pH of an aqueous formulation. Further, due to the low contact angle of the aqueous formulation to the glass, residues like liquid droplets may remain in a glass container after removing an aqueous formulation with, e.g., a syringe. In view of this, there have been attempts in the prior art to increase/optimize this "removable volume" from containers such as vials.

WO 00/15245 discloses a liquid formulation of highly concentrated botulinum toxin type B (about 2500 U/mL) that is stable when stored in glass vials at 5° C. for up to 30 months. However, this stability is only achieved by buffering the pH of the solution down to an acidic pH between 5 and 6, which causes pain upon injection.

Today, despite significant efforts in the art, there is still no packaging material available that allows for a safe, convenient and long-term storage of aqueous formulations of neurotoxins, in particular botulinum toxin. For this reason, lyophilization is still considered the best of all alternatives and, consequently, neurotoxins are generally manufactured in the form of lyophilized products, which are reconstituted prior to use.

Accordingly, materials suitable for packaging of aqueous formulations of neurotoxins that overcome the above disadvantages are highly sought after. In particular, there is a high demand for plastic materials having a reduced destabilizing effect on a neurotoxin in aqueous formulation, thereby providing an improved storage stability of neurotoxins.

OBJECTIVE OF THE INVENTION

In view of the above, the objective of the present invention is to provide a dosage form of a neurotoxin that has a long shelf-life, is convenient to use and inexpensive to produce.

SUMMARY OF THE INVENTION

The above object is solved by the provision of a vial that is at least partially filled with an aqueous formulation of a neurotoxin, which is characterized by a superior long-term stability of the neurotoxin. Further, the vial that is at least partially filled with an aqueous formulation of a neurotoxin is characterized in that it is convenient to use and inexpensive to produce.

In a first aspect, the present invention provides a vial that is at least partially filled with an aqueous formulation of a neurotoxin. The vial comprises a body having an open end, and a closed end. Further, the vial comprises a needle-penetrable member connected to said body and sealing the open end thereof. The needle-penetrable member and the body define an inner cavity that is at least partially filled with said aqueous formulation of a neurotoxin. Optionally, the vial comprises a cap mounted on said body and encompassing exposed surfaces of said needle-penetrable member. The body is made of a multilayer material comprising a first layer constituting the innermost layer. The first layer is at least partially in contact with the aqueous formulation of a neurotoxin. Further, the multilayer material comprises a second layer disposed on the first layer and a third layer disposed on the second layer so that the second layer is sandwiched between the first layer and the third layer. The first layer comprises or consists of cyclic olefin polymer (COP), cyclic olefin copolymer (COC) or a mixture thereof. The second layer comprises or consists of polyamide (PA), polyvinylidene chloride (PVDC), ethylene vinyl alcohol copolymer (EVOH) or any mixture thereof. The third layer comprises or consists of cyclic olefin polymer (COP), cyclic olefin copolymer (COC), polyester (PES), polyethylene terephthalate (PET), polyethylene (PE), high-density polyethylene (HDPE), polyvinyl chloride (PVC), polyvinylidene chloride (PVDC), medium-density polyethylene (MDPE), low-density polyethylene (LDPE), polypropylene (PP), polystyrene (PS), high impact polystyrene (HIPS), polyamides (PA) (nylons), acrylonitrile butadiene styrene (ABS), polyethylene/acrylonitrile butadiene styrene (PE/ABS), polycarbonate (PC), polycarbonate/acrylonitrile butadiene styrene (PC/ABS), polybutylene terephthalate (PBT), polyoxymethylene (POM), syndiotactic polystyrene (SPS), thermoplastic elastomers (TPE), polyphthalamide (PPA), poly (p-phenylene sulfide) (PPS), polyether ether ketone (PEEK), polyetherketone (PEK), polyamide-imide (PAI), polyphenylsulfone (PPSU), polysulfone (PSU), polycarbonate (PC), polycarbonate/polyethylene terephthalate blend (PC/PET), PCEM (poly[2-(9-carbazol-9-yl)ethyl methacrylate]), poly (methyl methacrylate) (PMMA), styrene-acrylonitrile resin (SAN), or any mixture or copolymer thereof.

In another aspect, the present invention provides a method for manufacturing said vial that is at least partially filled with an aqueous formulation of a neurotoxin. The method comprises the steps of a) providing a body as defined herein, b) filling the body at least partially with an aqueous formulation of a neurotoxin, and c) sealing the open end of the body with a needle-penetrable member.

In a further aspect, the present invention provides the use of a body as described herein for storing an aqueous formulation of a neurotoxin.

Further embodiments of the present invention are set forth in the appended dependent claims. The present invention may be more fully understood by reference to the following detailed description of the invention and the examples.

DETAILED DESCRIPTION OF A PREFERRED EMBODIMENT

The present invention is based on the surprising finding that an aqueous formulation of a neurotoxin, in particular botulinum toxin, is stable for a prolonged period of time at reduced temperature (e.g., 2 to 8° C.), at ambient temperature (e.g., 25° C.) and even at increased temperature (e.g., 30° C.), when stored in a vial as described herein.

In a first aspect, the present invention relates to a vial that is at least partially filled with an aqueous formulation of a neurotoxin. Preferably, the neurotoxin is botulinum toxin.

The vial comprises a body having an open end and a closed end. Preferably, the open end and the closed end are arranged opposite to each other.

The vial further comprises a needle-penetrable member connected to said body and sealing the open end thereof. The body and the needle-penetrable member define an inner cavity that is at least partially filled with said aqueous formulation of a neurotoxin. For example, the needle-penetrable member is a septum.

Optionally, the vial comprises a cap mounted on said body and encompassing exposed surfaces of said needle-penetrable member. Preferably, the cap is rotably mounted on said body.

The body is made of a multilayer material comprising a first layer constituting the innermost layer. The first layer is at least partially in contact with the aqueous formulation of a neurotoxin. The multilayer material further comprises a second layer disposed on the first layer and a third layer disposed on the second layer so that the second layer is sandwiched between the first layer and the third layer.

The first layer comprises or consists of cyclic olefin polymer (COP), cyclic olefin copolymer (COC) or a mixture thereof. The second layer comprises or consists of polyamide (PA), polyvinylidene chloride (PVDC), ethylene vinyl alcohol copolymer (EVOH) or any mixture thereof. The third layer comprises or consists of cyclic olefin polymer (COP), cyclic olefin copolymer (COC), polyester (PES), polyethylene terephthalate (PET), polyethylene (PE), high-density polyethylene (HDPE), polyvinyl chloride (PVC), polyvinylidene chloride (PVDC), medium-density polyethylene (MDPE), low-density polyethylene (LDPE), polypropylene (PP), polystyrene (PS), high impact polystyrene (HIPS), polyamides (PA) (nylons), acrylonitrile butadiene styrene (ABS), polyethylene/acrylonitrile butadiene styrene (PE/ABS), polycarbonate (PC), polycarbonate/acrylonitrile butadiene styrene (PC/ABS), polybutylene terephthalate (PBT), polyoxymethylene (POM), syndiotactic polystyrene (SPS), thermoplastic elastomers (TPE), polyphthalamide (PPA), poly(p-phenylene sulfide) (PPS), polyether ether ketone (PEEK), polyetherketone (PEK), polyamide-imide (PAI), polyphenylsulfone (PPSU), polysulfone (PSU), polycarbonate (PC), polycarbonate/polyethylene terephthalate blend (PC/PET), PCEM (poly[2-(9-carbazol-9-yl)ethyl methacrylate]), poly(methyl methacrylate) (PMMA), styrene-acrylonitrile resin (SAN), or any mixture or copolymer thereof.

The term "vial", as used herein, refers to any container with a seal. In particular, the vial has a tubular form or a bottle-like shape and is suitable for containing, storing, and/or transporting drug formulations. Preferably, the vial is stable to sterilization. Preferably, the vial is chemically inert. Preferably, the vial is a one-chamber vial. Preferably, the vial has a tubular form or a bottle-like shape comprising a central axis running from the open end to the closed end.

The term "partially filled", as used herein, means that less than 100% of the volume of the inner cavity defined by the body and the needle-penetrable member is occupied by the aqueous formulation of a neurotoxin. Or in other words: The inner cavity is not completely filled with the aqueous formulation of a neurotoxin. Thus, there remains a certain volume in the inner cavity that is not occupied by the aqueous formulation of a neurotoxin. This volume is also referred to as "headspace volume" and is typically occupied by a gas, for example air. Preferably, the headspace volume is occupied by an inert gas, for example nitrogen.

The term "aqueous formulation" or the term "aqueous formulation of a neurotoxin", as used herein, is intended to refer to an aqueous solution, suspension, dispersion or emulsion, and preferably refers to an aqueous solution. The "aqueous formulation" may comprise a buffer or may be free of a buffer. Preferred buffers are buffers that are active at about physiological pH, preferably at about pH=5.8 to 8.0, more preferably at about pH=6.0 to 7.5, more preferably at about pH=6.5 to 7.5, more preferably at about pH=6.8 to 7.2, even more preferably at about pH=7, such as a phosphate buffer.

Within the context of the present invention, the aqueous formulation of a neurotoxin may comprise various other pharmaceutically acceptable substances, for example, salts (e.g., sodium chloride), stabilizing proteins (e.g., albumin, gelatin), sugars (e.g., glucose, fructose, galactose, trehalose, sucrose and maltose), carbohydrate polymers (e.g., hyaluronic acid and polyvinylpyrollidone (PVP)), polyols (e.g. glycerol and sugar alcohols like mannitol, inositol, lactitol, isomalt, xylitol, erythritol, sorbitol), amino acids, vitamins (e.g. vitamin C), zinc, magnesium, anesthetic agents (e.g., local anesthetic agents like lidocaine), surfactants (e.g., Tween, polysorbates), and the like, either alone or in a combination thereof. The term "pharmaceutically acceptable", as used herein, refers to those compounds or substances which are suitable for contact with the tissues of mammals, especially humans.

The aqueous formulation of a neurotoxin may, in particular, comprise sodium chloride, preferably at a concentration of 0.01 to 2% (w/v) or 0.1 to 2.0% (w/v), more preferably at a concentration of 0.8 to 1.0% (w/v), and most preferably at a concentration of 0.9% (w/v).

The aqueous formulation of a neurotoxin may, in particular, comprise a stabilizing protein, especially an albumin (e.g. human serum albumin or bovine serum albumin), preferably human serum albumin (HSA). The concentration of the stabilizing protein (e.g. albumin, particularly human serum albumin) in the aqueous formulation of a neurotoxin may be from 0.01 to 10.0 mg/ml, from 0.01 to 5.0 mg/ml, from 0.05 to 5.0 mg/ml, from 0.1 to 2.0 mg/ml, from 0.2 to 2.0 mg/ml or from 0.2 to 1.5 mg/ml.

The aqueous formulation of a neurotoxin may, in particular, comprise a sugar, such as glucose, fructose, galactose, trehalose, sucrose and maltose, in particular lactose and sucrose, or a combination thereof. The concentration of the sugar, in particular of lactose or sucrose, in the aqueous formulation of a neurotoxin may range from 0.1 to 40 mg/ml, from 0.1 to 20 mg/ml, from 0.2 to 10 mg/ml or from 0.3 to 5 mg/ml.

The aqueous formulation of a neurotoxin may, in particular, comprise sodium chloride and a stabilizing protein such as human serum albumin, wherein, preferably, the concentration of the sodium chloride is 0.1-2.0% (w/v), in particular 0.8-1.0% (w/v) or 0.9% (w/v) and the concentration of the stabilizing protein is from 0.01 to 40 mg/ml, in particular from 0.01 to 10.0 mg/ml.

The aqueous formulation of a neurotoxin may, in particular, comprise sodium chloride, a stabilizing protein and a sugar selected from mono- and disaccharides, preferably in the concentrations as indicated in the preceding paragraphs. In particular, the aqueous formulation of a neurotoxin may comprise (i) sodium chloride, human serum albumin and lactose or (ii) sodium chloride, human serum albumin and sucrose or (iii) sodium chloride, human serum albumin, lactose and sucrose. Preferably, the concentration of the sodium chloride is 0.1-2.0% (w/v) (e.g., 0.8-1.0% (w/v), the concentration of the stabilizing protein is from 0.01 to 40.0 mg/ml (e.g., 0.01 to 10.0 mg/ml) and the concentration of the sucrose and/or lactose is from 0.1 to 40 mg/ml.

The aqueous formulation of a neurotoxin may be a reconstituted solution of Xeomin® or Bocouture® (Merz Pharmaceuticals GmbH), Botox® (Allergan, Inc.) or Dysport® (Ipsen, Ltd.), in particular wherein the reconstitution is carried out with an aqueous solution of 0.1 to 2.0% (w/v) sodium chloride, in particular 0.9% (w/v) (i.e. a physiological saline).

Preferably, the aqueous formulation of a neurotoxin has a pH of 6.0 to 7.5, 6.0 to 7.4, 6.0 to 7.3, 6.1 to 7.5 6.1 to 7.4, 6.5 to 7.5, 6.1 to 7.3, 6.2 to 7.2, 6.3 to 7.1, and 6.5 to 7.0. A pH within the range of 6.0 to 7.4 or 6.1 to 7.3 is advantageous.

The aqueous formulation of a neurotoxin may or may not contain any buffer such as a phosphate buffer, a phosphate-citrate buffer, a lactate buffer, an acetate buffer and the like. Furthermore, the aqueous formulation of a neurotoxin may be free of amino acids (e.g., methionine) and/or surfactants (e.g., polysorbates such as polysorbate 80). The aqueous formulation of a neurotoxin may also be, and is generally, preservative-free.

A preferred aqueous formulation of a neurotoxin for use herein comprises water, botulinum toxin (e.g., the neurotoxic component of botulinum toxin, preferably of type A), sodium chloride and human serum albumin, and may further optionally comprise a mono- or disaccharide, preferably lactose or sucrose.

Another preferred aqueous formulation of a neurotoxin for use herein comprises water, botulinum toxin (e.g., the neurotoxic component of botulinum toxin, preferably of type A) at a concentration such as 5 to 200 U/ml or 10 to 150 U/ml, a salt (e.g., sodium chloride) in a concentration such as 0.5% to 1.5% w/v, a sugar (e.g., a mono- or disaccharide, such as glucose, fructose, galactose, trehalose, sucrose and maltose) at a concentration such as 0.1% to 2% w/v, and a stabilizing protein (e.g., albumin) at a concentration such as 0.005% to 4% w/v, 0.01% to 3% w/v, or 0.1% to 1% w/v.

A further preferred aqueous formulation of a neurotoxin for use herein essentially consists of water, botulinum toxin (e.g. the neurotoxic component of botulinum toxin type A), sodium chloride, sucrose, and albumin (e.g., human serum albumin; HSA). The concentration of the mentioned components may be in the following ranges: 5 to 200 U/ml or 10 to 125 U/ml (botulinum toxin), 0.5% to 1.5% w/v or 0.7% to 1.1% w/v (sodium chloride), 0.1% to 2% w/v or 0.2% to 1% w/v (sucrose), 0.005% to 1% w/v, 0.01% to 0.5% w/v, 0.05% to 3% w/v or 0.1% to 1.5% w/v (HSA). A further preferred aqueous formulation of a neurotoxin for use herein is a Xeomin® solution, e.g., reconstituted with physiological saline (0.9% sodium chloride), including 5 to 200 U/ml of the neurotoxic component of botulinum toxin type A.

The term "essentially consists of", as used herein is intended to mean that substances other than those indicated are only contained in trace amounts, e.g. unavoidable impurities contained in the components used for formulating the aqueous formulation of a neurotoxin, and low amounts of impurities included in the isolated botulinum toxin (e.g., the neurotoxic component of botulinum toxin type A) as a result of the purification procedure (e.g., very low residual amounts of buffers, chelating agents and the like).

The term "neurotoxin" as used herein means any polypeptide that adversely affects cells of the nervous system, in particular any polypeptide that enters a neuron and inhibits neurotransmitter release. More specifically, the term "neurotoxin" encompasses any polypeptide produced by *Clostridium* bacteria (clostridial neurotoxins), i.e. any polypeptide produced by *Clostridium* bacteria (clostridial neurotoxins) which adversely affects cells of the nervous system, particularly which enters a neuron and inhibits neurotransmitter release. As used herein, a "neurotoxin" can be naturally occurring or recombinant. Within the context of the present invention, the neurotoxin is preferably botulinum toxin, in particular botulinum toxin of serotype A. The term "botulinum toxin", as used herein, refers to the botulinum toxin complex and/or the neurotoxic component, i.e. the pure neurotoxin polypeptide (sometimes referred to as the "150 kDa" polypeptide) without any associated nontoxic proteins.

In general, COP is prepared via ring-opening metathesis polymerization of cycloolefin followed by hydrogenation and COC is obtained through copolymerization of cycloolefin with ethylene or α-olefin.

COP and COC have been shown to be break-resistant, comprise a glass-like transparency and do not release alkali metal ions. Thus, COP and COC do not influence the pH of an aqueous formulation. Further, COP and COC comprise a very low amount of extractables and leachables and are considered inert with respect to neurotoxin-polymer-interactions. In particular, COP and COC usually show a low tendency for neurotoxin adsorption thereto.

The particular type of the COP or COC is not particularly limited. For example, just to mention a few, COC commercialized under the trade names APEL® by Mitsui or TOPAS® by "TOPAS Advanced Polymers GmbH" may be used. COP commercialized under the trade names Zeonex® and Zeonor® by Zeon and Arton® by Japan Synthetic Rubber may be used, among others. Preferably, COP commercialized under the trade name Zeonex 690 R is used.

Preferably, the first layer comprises or consists of COP. It is particularly preferred that the first layer consists of COP.

Preferably, the second layer comprises or consists of PA. It is particularly preferred that the second layer consists of PA. It has been shown that PA has a low oxygen permeability, which prevents the diffusion of oxygen from the surrounding into the vial thereby protecting the neurotoxin against oxidation and, thus, from degradation. The exact nature of the PA is not particularly limited. For example, just to mention a few, PA 6, PA 6.6, PA 11, PA 12, PA 69, PA 612, PA 46, and PA 6/12 may be used. Preferably, PA commercialized under the trade name Grivory G21, a polyamide 6I/6T copolymer (Nylon 6I/6T), is used.

According to another preferred embodiment, the second layer comprises or consists of PVDC, EVOH or a mixture thereof, which are also known to exhibit a low oxygen permeability. Preferably, the second layer consists of PVDC, EVOH or a mixture thereof.

Preferably, the third layer comprises or consists of COP. It is particularly preferred that the third layer consists of COP.

According to another preferred embodiment, the third layer may comprise or consist of cyclic olefin copolymer (COC), polyester (PES), polyethylene terephthalate (PET), polyethylene (PE), high-density polyethylene (HDPE), polyvinyl chloride (PVC), polyvinylidene chloride (PVDC), medium-density polyethylene (MDPE), low-density polyethylene (LDPE), polypropylene (PP), polystyrene (PS), high impact polystyrene (HIPS), polyamides (PA) (nylons), acrylonitrile butadiene styrene (ABS), polyethylene/acrylonitrile butadiene styrene (PE/ABS), polycarbonate (PC), polycarbonate/acrylonitrile butadiene styrene (PC/ABS), polybutylene terephthalate (PBT), polyoxymethylene (POM), syndiotactic polystyrene (SPS), thermoplastic elastomers (TPE), polyphthalamide (PPA), poly(p-phenylene sulfide) (PPS), polyether ether ketone (PEEK), polyetherketone (PEK), polyamide-imide (PAI), polyphenylsulfone (PPSU), polysulfone (PSU), polycarbonate (PC), polycarbonate/polyethylene terephthalate blend (PC/PET), PCEM (poly[2-(9-carbazol-9-yl)ethyl methacrylate]), poly(methyl methacrylate) (PMMA), styrene-acrylonitrile resin (SAN), or any mixture or copolymer thereof.

According to a preferred embodiment, the body is made of a multilayer material consisting of three layers, i.e. a first layer, a second layer and a third layer as described above.

According to a particularly preferred embodiment, the body is made of a multilayer material consisting of three layers and having the following layer sequence: COP-PA-COP.

For example, a Gx MultiShell® vial comprising a first COP layer, a second PA layer and a third COP layer commercially available from Gerresheimer Bünde GmbH may be used as body of the vial of the present invention.

As described above, the neurotoxin is preferably botulinum toxin. The botulinum toxin is not limited to a specific type of botulinum toxin. For example, botulinum toxin of serotypes A, B, C (including $C_1$, $C\alpha$, $C_2$ and $C\beta$), D, E, F, G and H may be used. Preferably, the neurotoxin is botulinum toxin of serotype A, B or E, particularly preferably of serotype A or B. For example, Xeomin® (incobotulinumtoxin; Merz Pharma GmbH & Co. KGaA), which contains the pure neurotoxic component of serotype A (i.e., the 150 kDa neurotoxic polypeptide) and which is devoid of any other proteins of the *Clostridium botulinum* toxin complex (i.e., the different hemagglutinis and the nontoxic, non-hemagglutinating protein), may be used. Further examples of botulinum toxin that may be used in the present invention are Botox® (onabotulinumtoxinA; Allergan, Inc.) or Dysport® (abobotulinumtoxinA; Ipsen Ltd.).

Preferably, the neurotoxin is present in the aqueous formulation at a concentration of 10 U/mL to 1000 U/mL, more preferably 10 U/mL to 200 U/ml, and most preferably 50 U/ml to 100 U/ml.

The needle-penetrable member may be a septum, a screw cap, a stopper of cork, plastic or rubber (lip closures and crimp closures), flip tops or snap caps. Preferably, the needle-penetrable member is a rubber stopper, wherein the rubber is preferably isoprene rubber (IS), butadiene rubber (e.g., polybutadiene, BR), butyl rubber (e.g., copolymer of isobutylene and isoprene, IIR), halogenated butyl rubber (e.g., chloro butyl rubber, CIIR; and bromo butyl rubber, BIIR), styrene-butadiene rubber (copolymer of styrene and butadiene, SBR) or a mixture thereof. Particularly preferably, the needle-penetrable member is a butyl rubber or a halogenated butyl rubber or a mixture thereof. Even more preferably, the needle-penetrable member is a bromo butyl rubber or a chloro butyl rubber, particularly preferably a bromobutyl rubber.

The needle-penetrable member may be uncoated, in particular not siliconized, or partially or fully coated, e.g. with a polymeric material. Within the present invention, the needle-penetrable member may be partially or fully siliconized. In particular, the needle-penetrable member may be partially or fully coated with crosslinked silicone. According to the present invention, the needle-penetrable member may be a halogenated butyl rubber (e.g. chloro or bromo butyl rubber) partially or fully coated with a silicone coating, in particular a crosslinked silicone coating. According to a particularly preferred embodiment, the needle-penetrable member is a bromobutyl rubber stopper comprising a coating of crosslinked silicone, which may cover a part of or the entire needle-penetrable member and preferably covers the entire needle-penetrable member. The needle-penetrable member may also contain colored ingredients, e.g. inorganic or organic dyes.

Preferably, the needle-penetrable member comprises or consists of a rubber material, preferably a rubber material as defined above.

For example, a Westar®RS stopper (rubber mixture 4023/50) may be used as a needle-penetrable member, which is a bromobutyl rubber stopper comprising a coating of cross-linked silicone.

The needle-penetrable member may also comprise or consists of polyamide (PA), polyvinylidene chloride (PVDC), ethyl vinyl alcohol copolymer (EVOH) or any mixture thereof. In this way, a potential oxygen intake through the needle-penetrable member can be limited.

According to a preferred embodiment, the multilayer material further comprises a fourth layer. The fourth layer is disposed on the third layer so that the third layer is sandwiched between the second layer and the fourth layer. The presence of the fourth layer protects the other layers and increases the mechanical stability of the vial.

Preferably, the fourth layer comprises or consists of cyclic olefin polymer (COP), cyclic olefin copolymer (COC), polyester (PES), polyethylene terephthalate (PET), polyethylene (PE), high-density polyethylene (HDPE), polyvinyl chloride (PVC), polyvinylidene chloride (PVDC), medium-density polyethylene (MDPE), low-density polyethylene (LDPE), polypropylene (PP), polystyrene (PS), high impact polystyrene (HIPS), polyamides (PA) (nylons), acrylonitrile butadiene styrene (ABS), polyethylene/acrylonitrile butadiene styrene (PE/ABS), polycarbonate (PC), polycarbonate/acrylonitrile butadiene styrene (PC/ABS), polybutylene terephthalate (PBT), polyoxymethylene (POM), syndiotactic polystyrene (SPS), thermoplastic elastomers (TPE), polyphthalamide (PPA), poly(p-phenylene sulfide) (PPS), polyether ether ketone (PEEK), polyetherketone (PEK), polyamide-imide (PAI), polyphenylsulfone (PPSU), polysulfone (PSU), polycarbonate (PC), polycarbonate/polyethylene terephthalate blend (PC/PET), PCEM (poly[2-(9-carbazol-9-yl)ethyl methacrylate]), poly(methyl methacrylate) (PMMA), styrene-acrylonitrile resin (SAN), or any mixture or copolymer thereof.

When the multilayer material comprises a fourth layer as described above, the third layer and the fourth layer preferably do not consist of the same material.

According to a preferred embodiment, the vial comprises an outer surface that is in contact with the surrounding and that comprises an antimicrobial substance.

Preferably, the antimicrobial substance comprises elemental silver or a silver-comprising compound, elemental copper or a copper-comprising compound, elemental zinc or a zink-comprising compound, elemental titanium or a titanium-comprising compound, elemental molybdenum or a molybdenum-comprising compound, elemental tungsten or a tungsten-comprising compound, an organic antimicrobial compound or a mixture thereof. Preferably, the antimicrobial substance is selected from colloidal silver, a silver salt (e.g. AgCl or $AgNO_3$), silver oxide, $TiO_2$, $MoO_3$, $MoO_2$, $ZnMoO_4$, $Mo_2N$, MoC, $MoSi_2$, $MoS_2$, WC, WN, $WSi_2$, $WO_3$, triclosan, polyhexanide or any mixture thereof.

By means of providing the outer surface of the vial with an antimicrobial substance, the presence of microorganisms, in particular pathogenic microorganisms, which may be present on the outer surface of the vial is significantly minimized, if not totally avoided. Pathogenic microorganisms adhering to the outer surface of the vial pose a potential source of contamination as these microorganisms may accidentally be introduced into the aqueous formulation of a neurotoxin. This may for example happen, when a user (e.g., a physician) first accidentally touches the outer surface of the vial with a needle and then introduces the same needle into the vial through the needle-penetrable member. Thus, the risk of contamination can be significantly reduced by providing the outer surface of the vial with an antimicrobial substance.

According to a preferred embodiment, the inner cavity is partially filled with the aqueous formulation and further comprises a gas or a gaseous mixture, i.e. the inner cavity comprises a "headspace volume" that is occupied by a gas or a gaseous mixture. The gas or gaseous mixture comprises at least 80%, preferably at least 90%, more preferably at least 93%, more preferably at least 95%, more preferably at least 99%, more preferably more than 99% of an inert gas. The inert gas is preferably selected from nitrogen and argon, more preferably nitrogen.

Since an equilibrium between gases dissolved in the aqueous formulation and gases present in the "headspace volume" will be formed over time, oxygen present in the aqueous formulation will diffuse from the aqueous formulation into the "headspace volume" and inert gas present in the "headspace volume" will diffuse into the aqueous formulation. In this way, the amount of oxygen in the aqueous formulation is reduced, thereby further protecting the neurotoxin against oxidation.

Preferably, the aqueous formulation of a neurotoxin comprises less than 20%, preferably less than 15%, more preferably less than 10%, more preferably less than 5%, more preferably less than 3%, more preferably less than 2%, more preferably less than 1%, of oxygen. The percentages are relative to the maximum amount of oxygen soluble in the aqueous formulation at 25° C. and normal pressure (about 1.013 bar), as measured at 25° C. and normal pressure. The amount of oxygen dissolved in the aqueous formulation of a neurotoxin is determined according to ASTM D888-18.

Preferably, the vial has a total volume of 1.0 to 20.0 mL, more preferably 2.0 to 18.0 mL, more preferably 5.0 to 15.0 mL, more preferably 7.0 to 12.0 mL, more preferably 8.0 to 11.0 mL, more preferably 8.5 to 9.5 mL, more preferably 9.0 to 9.5 mL, and most preferably about 9.4 mL. According to another preferred embodiment, the vial has a total volume of 1.0 to 3.0 mL, preferably about 2.0 mL. Total volume means the total volume of the vial body including the neck portion, if present.

Preferably, the body has a neck portion comprising the open end and a bottom portion connected to said neck portion comprising the closed end, wherein the neck portion is at least partially free of the aqueous formulation and the bottom portion comprises the aqueous formulation. Preferably, the neck portion is totally free of the aqueous formulation. In this embodiment, the neck portion is preferably occupied with an inert gas as described above. This is further advantageous, because the neck portion usually accommodates the needle-penetrable member as defined above and, thus, contacts between the aqueous formulation and the needle-penetrable member are avoided in an upright or slightly tilted orientation of the vial. Preferably, the minimal inner diameter of the neck portion is less than 80%, preferably less than 75%, more preferably less than 70%, more preferably less than 60%, more preferably less than 50%, more preferably less than 40% of the maximal inner diameter of the bottom portion. It is particularly preferred that the minimal inner diameter of the neck portion is from 55% to 80%, more preferably 60% to 80%, more preferably 60% to 75%, more preferably 65% to 70%, and most preferably 66% to 68% of the maximal inner diameter of the bottom portion.

This geometry of a narrow neck portion leads to the effect that the aqueous formulation is essentially remained in the bottom portion even when the vial is slightly shaken, tilted or the like. Thus, the contact between the aqueous formulation and the needle-penetrable member is minimized. Contacts between the aqueous formulation and the needle-penetrable member may be particularly disadvantageous if the needle-penetrable member comprises extractables or leachables or otherwise destabilizes the neurotoxin.

A preferred embodiment of the vial at least partially filled with an aqueous formulation of a neurotoxin according to the present invention comprises: a body having an open end and a closed end; a needle-penetrable member connected to said body and sealing the open end thereof, the needle-penetrable member and the body defining an inner cavity that is at least partially filled with said aqueous formulation of a neurotoxin; and optionally, a cap mounted on said body and encompassing exposed surfaces of said needle-penetrable member; wherein the body is made of a multilayer material comprising a first layer constituting the innermost layer that is at least partially in contact with the aqueous formulation of a neurotoxin, a second layer disposed on the first layer, and a third layer disposed on the second layer so that the second layer is sandwiched between the first layer and the third layer; wherein the first layer comprises or consists of cyclic olefin polymer (COP), the second layer comprises or consists of polyamide (PA), and the third layer comprises or consists of cyclic olefin polymer (COP), and wherein the aqueous formulation of a neurotoxin is as defined hereinabove, and may be an aqueous botulinum toxin formulation comprising water, botulinum toxin, sodium chloride and human serum albumin or an aqueous botulinum toxin formulation comprising water, botulinum toxin, sodium chloride, human serum albumin and lactose and/or sucrose.

A preferred embodiment of the vial at least partially filled with an aqueous formulation of a neurotoxin according to the present invention comprises: a body having an open end and a closed end; a needle-penetrable member connected to said body and sealing the open end thereof, the needle-penetrable member and the body defining an inner cavity that is at least partially filled with said aqueous formulation of a neurotoxin; and optionally, a cap mounted on said body and encompassing exposed surfaces of said needle-penetrable member; wherein the body is made of a multilayer material comprising a first layer constituting the innermost layer that is at least partially in contact with the aqueous formulation of a neurotoxin, a second layer disposed on the first layer, and a third layer disposed on the second layer so that the second layer is sandwiched between the first layer and the third layer; wherein the first layer comprises or consists of cyclic olefin polymer (COP), the second layer comprises or consists of polyamide (PA), and the third layer comprises or consists of cyclic olefin polymer (COP), and wherein the aqueous formulation of a neurotoxin is as defined hereinabove, and may be an aqueous botulinum toxin formulation comprising water, botulinum toxin, sodium chloride and human serum albumin or an aqueous botulinum toxin formulation comprising water, botulinum toxin, sodium chloride, human serum albumin and lactose and/or sucrose, wherein said needle-penetrable member is as defined above, and may be a bromobutyl rubber stopper comprising a coating of crosslinked silicone.

In a second aspect, the present invention relates to a method for manufacturing the vial at least partially filled with an aqueous formulation of a neurotoxin of the first aspect.

The method comprises at least the following steps:

a) providing a body as defined above, b) filling the body at least partially with an aqueous formulation of a neurotoxin, and c) sealing the open end of the body with a needle-penetrable member.

Preferably, the body is filled with an inert gas, preferably nitrogen or argon, more preferably nitrogen, prior to step b).

If the body is partially filled with the aqueous formulation of a neurotoxin, the "headspace volume" may be filled with an inert gas, preferably nitrogen or argon, after step b).

Also preferably, the aqueous formulation of a neurotoxin is degassed or saturated with an inert gas, preferably nitrogen or argon, more preferably nitrogen, prior to step b) or step c).

Optionally, the method comprises a step d) of mounting a cap on the body so that the cap encompasses exposed surfaces of the needle-penetrable member.

In a third aspect, the present invention relates to the use of a body as described in the first aspect for storing an aqueous formulation of a neurotoxin, preferably botulinum toxin.

Preferably, the body is used for storing an aqueous formulation of a neurotoxin for a period of more than 3 months, preferably more than 6 months, more preferably more than 9 months, more preferably more than 12 months, more preferably more than 15 months, more preferably more than 18 months, and more preferably more than 24 months, wherein the storage temperature may be refrigerator temperature (i.e. 2° C. to 8° C.) or standard test temperature of 25+1-2° C. It has been shown that the aqueous formulation of a neurotoxin, in particular botulinum toxin, is stable at these temperature conditions for long periods of time, wherein "stable" is defined as a loss of toxin activity, relative to the initial activity at the beginning of the storage period, of 20% or less, in particular 15% or less or 10% or less. The toxin activity may be determined by a suitable potency method, e.g., a cell based assay as disclosed in WO 2013/049508 and WO 2014/207109.

The present invention will now be further illustrated by the following, non-limiting examples.

Examples

The following examples show that, contrary to expectation and common belief in the art, an aqueous formulation of a neurotoxin, in particular botulinum toxin, stored in a vial as defined herein exhibits an excellent stability for a prolonged time period at a standard refrigerator temperature (2 to 8° C.), standard test temperature (25° C.) and even increased temperature (30° C.).

Materials and Methods

An aqueous botulinum toxin formulation was prepared by reconstituting a commercially available 100U Xeomin® composition by using 0.9% sodium chloride solution.

The pH of the Xeomin® formulation was set to above 8.

The activity of the Xeomin® formulation after storage for a certain amount of time was determined by using a cell-based assay as disclosed in WO 2013/049508 and WO 2014/207109.

Results

The results of the stability test are shown in Table 1 below:

TABLE 1

Results of the stability test (results in % of $t_0$)

| Xeomin formulation stored in . . . | Initial ($t_0$) | 3 months at 25° C. | 6 months at 25° C. | 3 months at 2-8° C. | 1 months at 30° C. | 3 months at 30° C. |
|---|---|---|---|---|---|---|
| . . . standard glass vial[1] | 100% | 88% | 77% | 96% | 86% | 84% |
| . . . plastic vial[2] | 100% | 85% | 72% | 90% | 85% | 79% |
| . . . Gx MultiShell® vial[3] | 100% | 101% | 90% | 94% | 104% | 87% |

[1]Total volume = 9 mL
[2]Mono-COP vial commercially available from Gerresheimer Bünde GmbH
[3]Commercially available from Gerresheimer Bünde GmbH
All vials were closed with a Westar ®RS stopper (rubber mixture 4023/50).

As it is evident from Table 1, the Xeomin® formulation is stable for a prolonged period of time at reduced temperature (e.g., 2 to 8° C.), at ambient temperature (e.g., 25° C.) and even at increased temperature (e.g., 30° C.), when stored in a vial as described herein. For example, while the activity of the Xeomin® formulation is reduced to 77% and 72% upon storage for 6 months at 25° C. in a standard glass vial and a plastic vial, respectively, the Xeomin® formulation shows an activity of 90% when stored at the same conditions in a Gx MultiShell® vial. This is particularly surprising since highly destabilizing conditions of a pH >8 were present. If the vial is stored at 30° C. for 1 and 3 months, similarly improved storage stability is observed.

The invention claimed is:

1. A vial at least partially filled with an aqueous formulation of botulinum toxin, the vial comprising:
   a body having an open end and a closed end;
   a needle-penetrable member connected to said body and sealing the open end thereof, the needle-penetrable member and the body defining an inner cavity that is at least partially filled with said aqueous formulation of botulinum toxin; and
   optionally, a cap mounted on said body and encompassing one or more exposed surfaces of said needle-penetrable member;
   wherein the body is made of a multilayer material comprising a first layer constituting an innermost layer that is at least partially in contact with the aqueous formulation of botulinum toxin, a second layer disposed on the first layer, and a third layer disposed on the second layer so that the second layer is sandwiched between the first layer and the third layer; and
   wherein the first layer comprises or consists of cyclic olefin polymer (COP), cyclic olefin copolymer (COC) or a mixture thereof,
   the second layer comprises or consists of polyamide (PA), and
   the third layer comprises or consists of cyclic olefin polymer (COP), cyclic olefin copolymer (COC), polyester (PES), polyethylene terephthalate (PET), polyethylene (PE), high-density polyethylene (HDPE), polyvinyl chloride (PVC), polyvinylidene chloride (PVDC), medium-density polyethylene (MDPE), low-density polyethylene (LDPE), polypropylene (PP), polystyrene (PS), high impact polystyrene (HIPS), polyamides (PA) (nylons), acrylonitrile butadiene styrene (ABS), polyethylene/acrylonitrile butadiene styrene (PE/ABS), polycarbonate (PC), polycarbonate/acrylonitrile butadiene styrene (PC/ABS), polybutylene terephthalate (PBT), polyoxymethylene (POM), syndiotactic polystyrene (SPS), thermoplastic elastomers (TPE), polyphthalamide (PPA), poly(p-phenylene sulfide) (PPS), polyether ether ketone (PEEK), polyetherketone (PEK), polyamide-imide (PAI), polyphenylsulfone (PPSU), polysulfone (PSU), polycarbonate (PC), polycarbonate/polyethylene terephthalate blend (PC/PET), PCEM (poly[2-(9-carbazol-9-yl)ethyl methacrylate]), poly(methyl methacrylate) (PMMA), styrene-acrylonitrile resin (SAN), or any mixture or copolymer thereof.

2. The vial according to claim 1, wherein said needle-penetrable member comprises or consists of polyamide (PA), polyvinylidene chloride (PVDC), ethylene vinyl alcohol copolymer (EVOH), isoprene rubber (IS), butadiene rubber, butyl rubber, halogenated butyl rubber, styrene-butadiene rubber, and mixtures thereof, optionally of a butyl rubber or a halogenated butyl rubber or a mixture thereof, optionally of a bromo butyl rubber or a chloro butyl rubber.

3. The vial according to claim 1, wherein the multilayer material further comprises a fourth layer disposed on the third layer so that the third layer is sandwiched between the second layer and the fourth layer.

4. The vial according to claim 3, wherein the fourth layer comprises or consists of cyclic olefin polymer (COP), cyclic olefin copolymer (COC), polyester (PES), polyethylene terephthalate (PET), polyethylene (PE), high-density polyethylene (HDPE), polyvinyl chloride (PVC), polyvinylidene chloride (PVDC), medium-density polyethylene (MDPE), low-density polyethylene (LDPE), polypropylene (PP), polystyrene (PS), high impact polystyrene (HIPS), polyamides (PA) (nylons), acrylonitrile butadiene styrene (ABS), polyethylene/acrylonitrile butadiene styrene (PE/ABS), polycarbonate (PC), polycarbonate/acrylonitrile butadiene styrene (PC/ABS), polybutylene terephthalate (PBT), polyoxymethylene (POM), syndiotactic polystyrene (SPS), thermoplastic elastomers (TPE), polyphthalamide (PPA), poly(p-phenylene sulfide) (PPS), polyether ether ketone (PEEK), polyetherketone (PEK), polyamide-imide (PAI), polyphenylsulfone (PPSU), polysulfone (PSU), polycarbonate (PC), polycarbonate/polyethylene terephthalate blend (PC/PET), PCEM (poly[2-(9-carbazol-9-yl)ethyl methacrylate]), poly(methyl methacrylate) (PMMA), styrene-acrylonitrile resin (SAN), or any mixture or copolymer thereof.

5. The vial according to claim 1, comprising an outer surface that is in contact with surroundings, wherein the outer surface comprises an antimicrobial substance.

6. The vial according to claim 5, wherein the antimicrobial substance comprises elemental silver or a silver-comprising compound, elemental copper or a copper-comprising compound, elemental zinc or a zinc-comprising compound, elemental titanium or a titanium-comprising compound, elemental molybdenum or a molybdenum-comprising compound, elemental tungsten or a tungsten-comprising compound, an organic antimicrobial compound, or any combination thereof.

7. The vial according to claim 1, wherein the inner cavity is partially filled with the aqueous formulation of botulinum toxin and further comprises a gas or a gaseous mixture, wherein the gas or gaseous mixture comprises at least 80% of an inert gas, optionally nitrogen or argon.

8. The vial according to claim 1, wherein the aqueous formulation comprises less than 20% of oxygen, relative to the maximum amount of oxygen soluble in the aqueous formulation at 25° C. and normal pressure (about 1.013 bar), as measured at 25° C. and normal pressure.

9. The vial according to claim 1, wherein the body has a neck portion comprising the open end and a bottom portion connected to said neck portion and comprising the closed end, wherein the neck portion is at least partially free of the aqueous formulation, optionally totally free of the aqueous formulation, and the bottom portion comprises the aqueous formulation.

10. The vial according to claim 1, wherein the botulinum toxin is present in the aqueous formulation at a concentration of 10 U/ml to 1000 U/mL.

11. A method for manufacturing a vial at least partially filled with an aqueous formulation of botulinum toxin, according to claim 1, comprising:
    a) providing a body as defined in claim 1,
    b) filling the body at least partially with an aqueous formulation of botulinum toxin, and
    c) sealing the open end of the body with a needle-penetrable member.

12. The method according to claim 11, wherein the body is filled with an inert gas, optionally nitrogen or argon, prior to b).

13. The method according to claim 11, wherein the aqueous formulation of botulinum toxin is degassed or saturated with an inert gas, optionally nitrogen or argon, prior to b) or c).

14. A product comprising a body as defined in claim 1 for storing an aqueous formulation of botulinum toxin.

* * * * *